United States Patent
Advenier et al.

(12)

(10) Patent No.: US 6,310,050 B1
(45) Date of Patent: Oct. 30, 2001

(54) THERAPEUTIC USE OF COMPOUNDS WITH $\beta_3$-AGONIST ACTIVITY

(75) Inventors: Charles Advenier, Paris (FR); Luciano Manara, Pietra Morazzi (IT)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/807,342

(22) PCT Filed: Sep. 29, 1999

(86) PCT No.: PCT/FR99/02308

§ 371 Date: May 24, 2001

§ 102(e) Date: May 24, 2001

(87) PCT Pub. No.: WO00/21508

PCT Pub. Date: Apr. 20, 2000

(30) Foreign Application Priority Data

Oct. 14, 1998 (FR) .................................................. 98 12877

(51) Int. Cl.[7] ........................ A61K 31/675; A61K 31/44; A61K 31/425; A61K 31/415; A61K 31/40

(52) U.S. Cl. ............................ 514/81; 514/338; 514/340; 514/365; 514/387; 514/419; 514/539; 514/597; 514/605; 514/652

(58) Field of Search ............................... 514/81, 338, 340, 514/365, 387, 419, 539, 597, 605, 652

(56) References Cited

U.S. PATENT DOCUMENTS 5,488,151   1/1996   Baroni et al. .

FOREIGN PATENT DOCUMENTS 0626367   11/1994   (EP) .

OTHER PUBLICATIONS

Manara et al., British Journal of Pharmacology (1996), 117, 435–442.

Bardou et al., European Journal of Pharmacology 353 (1998), 281–287.

*Primary Examiner*—Raymond Henley, III
(74) *Attorney, Agent, or Firm*—Michael D. Alexander

(57) ABSTRACT

The invention relates to the method of use of compounds with $B_3$-agonist activity for inhibiting uterine contractions, preventing or slowing down premature labor, or for the treatment and/or prophylaxis of dysmenorrhea.

6 Claims, No Drawings

THERAPEUTIC USE OF COMPOUNDS WITH β₃-AGONIST ACTIVITY

This is a 371 of PCT/FR99/02308 filed Sep. 29, 1999.

A subject matter of the present invention is a novel use of compounds which are active with respect to the β₃-adrenergic receptor. The invention more particularly relates to the use of β₃-agonists in the preparation of medicaments which inhibit uterine contractions.

The β₃-adrenergic receptor, also sometimes indicated as atypical β receptor, is mainly located in the adipose tissue and in the gastrointestinal tract.

Numerous patent applications have been published in recent years disclosing novel products having β₃-agonist activity.

The products are indicated in several pathologies, such as obesity, diabetes, hyperglycemia or disorders of the gastrointestinal apparatus. To date, no patent application or scientific publication has envisaged the possibility of using compounds having a β₃-agonist activity as inhibitors of uterine contraction in order to obtain a beneficial effect in the event of dysmenorrhea or a tocolytic activity.

The products normally used as tocolytic agents are β₂-agonists and in particular ritodrine and salbutamol.

It is known that, because of the effects at the pulmonary or cardiac level caused by all β₂-agonists, the use of ritodrine or salbutamol often results in significant side effects.

For the treatment of dysmenorrhea, the products normally used are nonsteroidal antiinflammatories, which have well known side effects, in particular at the gastric level.

β₃-Adrenergic compounds were initially tested in the rat and it is only in recent years that researchers have developed tests for evaluating the activity of these compounds in human tissues.

Croci et al. report that selective β₃-agonists, such as N-[(6-hydroxy-1,2,3,4-tetrahydronaphth-2-yl)methyl]-2-hydroxy-2-(3-chlorophenyl)ethanamine and N-[(7-methoxy-1,2,3,4-tetrahydronaphth-2-yl)methyl]-2-hydroxy-2-(3-chlorophenyl)ethanamine, are inactive with respect to the uterus of the rat (Br. J. Pharmacol., 116, Proc. Suppl., 204 P. 1995).

In the same way, Landi et al. show that N-[(2S)-7-carboxymethoxy-1,2,3,4-tetrahydronaphth-2-yl]-(2R)-2-(3-chlorophenyl)-2-hydroxyethanamine, a selective β₃-agonist, does not have activity with respect to the uterus of the rat (Br. J. Pharmacol., 114, Proc. Suppl., 432P, 1995).

The activity which some β₃-agonists exhibit with respect to the rat uterus is in fact to be attributed to their low selectivity with respect to β₂-receptors (J. Pharmacol. Exp. Ther., 277, I, 22–27, 1996).

We have now found, in an entirely surprising fashion, that β₃-agonists cause a relaxant effect on the muscles of the human uterus.

Thus, according to one of its aspects, a subject matter of the present invention is the use of a selective β₃-agonist in the preparation of a medicament which inhibits uterine contractions in human beings.

More particularly, a subject matter of the invention is the use of a selective β₃-agonist in the preparation of a medicament intended to treat dysmenorrhea or which has a tocolytic effect.

The β₃-agonists which are a subject matter of the present invention are, for example, the products included in the following patents or patent applications: EP 436 435, EP 500 443, WO 98/20005, JP 10007647, US 5 705 515, EP 822 185, WO 97/46556, WO 97/43273, JP 09268171, FR 2 746 395, WO 97/37646, EP 801 060, WO 97/34905, WO 97/25311, WO 97/21666, WO 97/21665, JP 09118655, WO 97/15549, GB 2 305 665, EP 764 640, EP 764 632, WO 96/35671, WO 96/35685, JP 08259558, US 5 561 142, JP 08198866, JP 08165276, JP 08157470, EP 714 883, WO 96/16938, WO 96/04234, WO 96/04233, US 5 488 064, US 5 491 134, US 5 482 971, WO 95/29159, WO 95/33724, ZA 9409874, JP 07228543, WO 95/25104, EP 659 737, WO 95/11223, WO 95/08527, WO 95/07284, JP 07112958, WO 95/04047, JP 06345731, WO 94J29290, JP 06293664, WO 94/24090, EP 611 003, EP 608 568, WO 94/12166, US 5 321 036, WO 93/22277, WO 94/02493, EP 565 317, WO 93/15041 and WO 94/16938.

Advantageous β₃-agonists according to the present invention are represented by the formula (I):

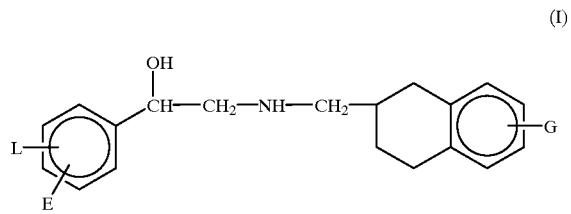

(I)

in which

E represents hydrogen, a (C₁–C₄)alkyl group, a (C₁–C₄) alkoxy group, a phenyl group, a nitro group, a halogen atom or a trifluoromethyl group, L represents hydrogen, a (C₁–C4)alkyl group, a (C₁–C₄) alkoxy group, a phenyl group, a nitro group or a halogen atom, or E and L together represent a —CH=CH—CH=CH— or —CH₂—CH₂—CH₂—CH₂— group, and G represents hydrogen, a chlorine atom, a hydroxyl group or an OG' group where G' represents a (C₁–C₄)alkyl group which is unsubstituted or substituted by a hydroxyl, (C₁–C₄)alkoxy, (C₁–C₄)alkoxycarbonyl, carboxyl or (C₃–C₇)cycloalkyl group; a (C₃–C₇) cycloalkyl group; or a (C₂–C₄)alkanoyl group, and their pharmaceutically acceptable salts, disclosed in EP 0 436 435 as intestinal spasmolytics.

Among the compounds of formula (I), N-[(6-hydroxy-1,2,3,4-tetrahydronaphth-(2R)-2-yl)methyl]-(2R)-2-hydroxy-2-(3-chlorophenyl)ethanamine, N-[(7-methoxy-1,2,3,4-tetrahydronaphth-(2R)-2-yl)methyl]-(2R)-2-hydroxy-2-(3-chlorophenyl)ethanamine and their pharmaceutically acceptable salts are particularly advantageous compounds.

Other advantageous β₃-agonists according to the present invention are the following compounds:

the product L-755507, disclosed in EP 611 003, of formula (a):

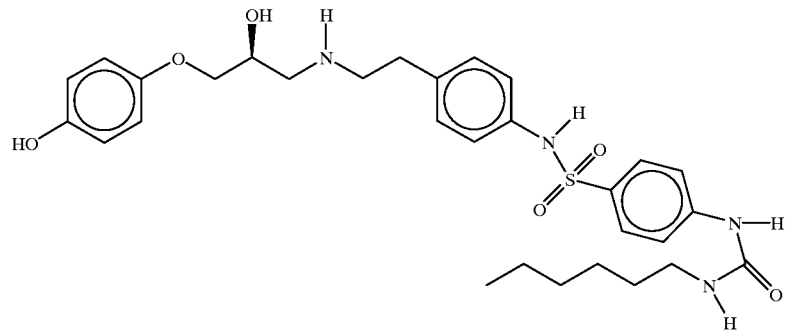
the product L-750355, disclosed in EP 611 003, of formula (b):
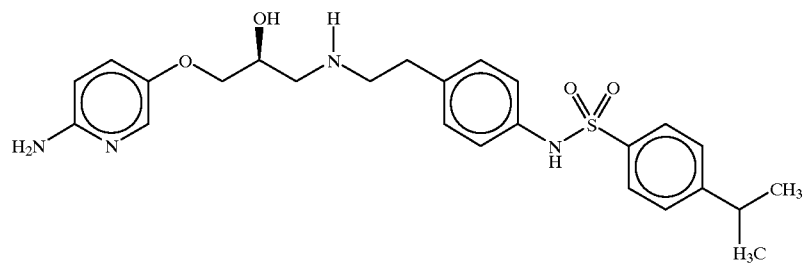
the product L-759574, disclosed in EP 611 003, of formula (c):
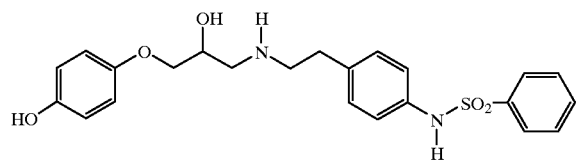
the product, disclosed in WO 95/29159, of formula (d):
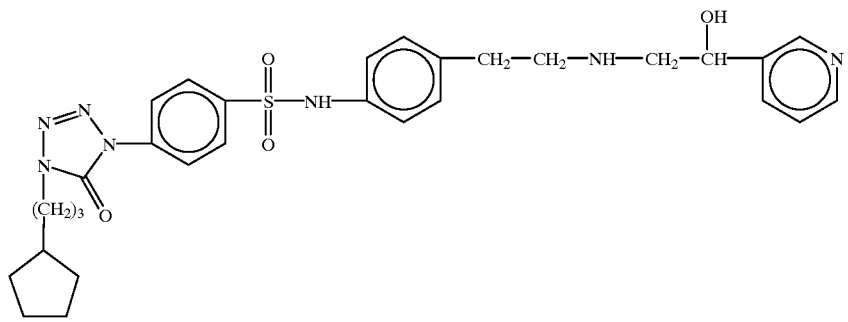

the product, disclosed in WO 95/04047, of formula (e):

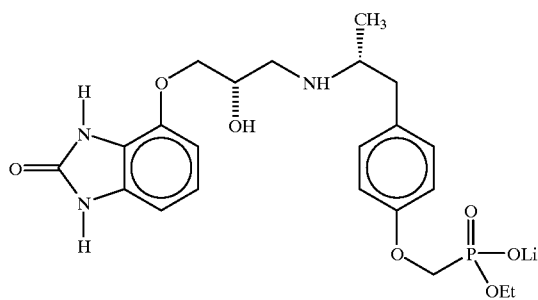

the product, disclosed in WO 96/04233, of formula (f):

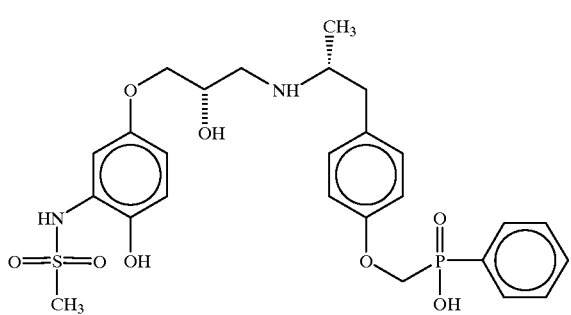

the product, SB-226552, disclosed in WO 96/04233, of formula (g):

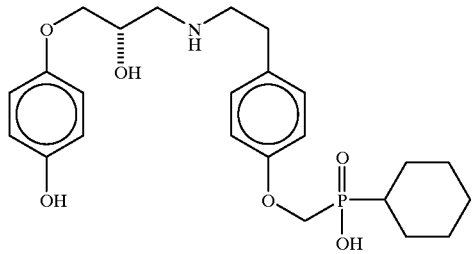

the product, disclosed in EP 764 640, of formula (h):

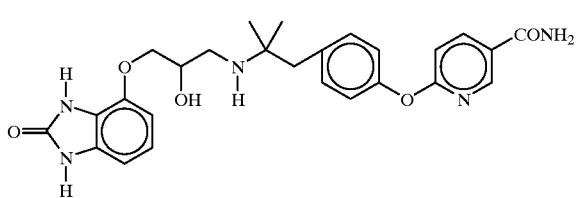

the product, CP-331679, disclosed in WO 94/29290, of formula (i):

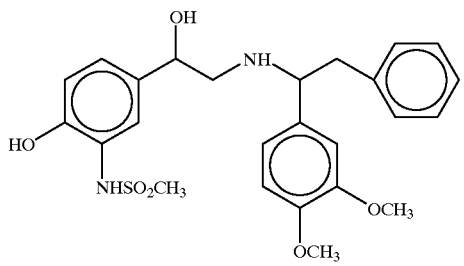

the product disclosed in EP 659 737, of formula (j):

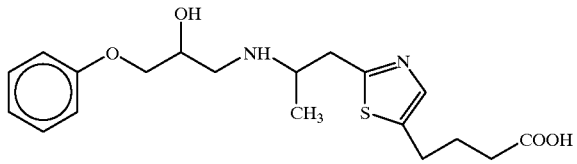

the product BMS 187257, disclosed in US 5 321 036, of formula (k):

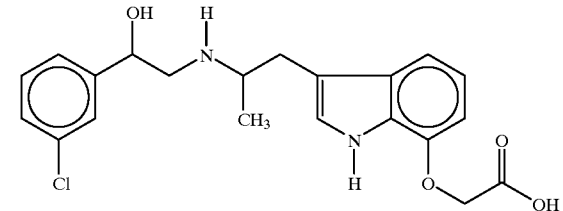

the product AD-9677, disclosed in WO 94/16938, of formula (l):

the product FR-149175, disclosed in WO 93/15041, of formula (m):

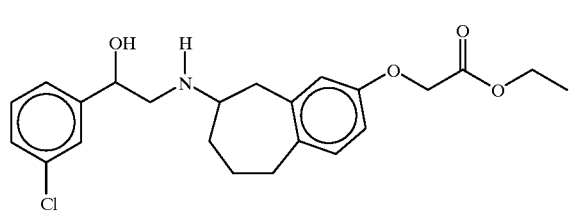

According to another of its aspects, a subject matter of the present invention is a method for inhibiting uterine contractions, characterized in that an effective dose of a β₃-agonist compound is administered to patients requiring said treatment.

The activity of the compounds was demonstrated by measuring the inhibition of spontaneous contractions on human uterus samples.

The β₃-agonists tested, in particular N-[(6-hydroxy-1,2,3,4-tetrahydronaphth-2-yl)methyl]-2-hydroxy-2-(3-chlorophenyl)ethanamine and N-[(7-methoxy-1,2,3,4-tetrahydronaphth-2-yl)methyl]-2-hydroxy-2-(3-chlorophenyl)ethanamine, showed an ability to inhibit contractions of the uterus similar to that of salbutamol, a product having a β₂-agonist activity, which exerts a tocolytic effect by virtue of this activity (Fundam. Clin. Pharmacol., 1995, 9 (4), 407).

In addition, it was confirmed that the inhibition of uterine contraction brought about by the compounds of the invention is not blocked by the addition of a β₂-agonist, such as propanolol, which demonstrates that this tocolytic activity cannot be attributed to an effect on the β₂ receptor.

Tests of inhibition of uterine contractions

Preparation of tissues from the human myometrium

Tissues from the myometrium were obtained from women with normal pregnancies nearly at term without complications (between the 38th and 40th weeks of gestation) but who have to undergo a cesarean operation. Samples of tissues were excized from the longitudinal layer of the corpus uteri, on the site away from the placenta, and immediately placed in Krebs solution at 4° C. (composition in mM: NaCl 118, KCl 5.4, CaCl₂ 2.5, KH₂PO₄ 0.6, MgSO₄ 1.2, NaHCO₃ 25, glucose 11.7). The tissues were dissected without serous membrane and used fresh. The use of the tissue from the human myometrium for tests was approved by the local ethics committee.

Functional study

Tissues from the myometrium, for each piece of muscle, were cut into 6–8 strips (8–10 mm in length and 2–3 mm in cross section) and suspended isometrically under a resting tension of 2 g in a 20 ml organ bath comprising a Krebs solution (composition as above) at 37° C. and aerated with 95% of O₂ and 5% of CO₂ (pH 7.40). After an hour, during which the strips from the myometrium were washed every quarter of an hour and the resting tension adjusted to 2 g, the strips were left to equilibrate for an additional hour until the moment when they showed a regular spontaneous rhythmic contractile activity. The changes in tension were measured by means of Pioden strain gauges (UFI), amplified (EMKA; France) and recorded (Linseis L65514; Germany). Once the amplitude of the contractions became regular, the cumulative concentration/response curves for inhibition (from $10^{-8}$ to $3 \times 10^{-5}$ M) were determined for each compound studied: salbutamol, N-[(6-hydroxy-1,2,3,4-tetrahydronaphth-2-yl)methyl]-2- hydroxy-2-(3-chlorophenyl)ethanamine and N-[(7-methoxy-1,2,3,4-tetrahydronaphth-2-yl)methyl]-2-hydroxy-2-(3-chlorophenyl)ethanamine, Each medicament was tested on 2–24 preparations, each originating from a different patient. Control tests were carried out using solvent. The effect of each relaxation agent was expressed as a percentage of the maximum inhibition obtained on adding theophylline ($3 \times 10^{-3}$ M) at the end of the test. In the above test, the compounds N-[(6-hydroxy-1,2,3,4-tetrahydronaphth-2-yl)methyl]-2-hydroxy-2-(3-chlorophenyl)ethanamine and N-[(7-methoxy-1,2,3,4-tetranhydronaphth-2-yl)methyl]-2-hydroxy-2-(3chlorophenyl)ethanamine showed activity equivalent to that of salbutamol.

By virtue of this effect on the human uterus, the compounds of the invention can advantageously be used in the preparation of medicaments capable of preventing or slowing down premature labor or for slowing down or halting labor for a brief period of time sufficient to give other forms of care.

Furthermore, the compounds of the invention can indeed be used for the prevention and/or the treatment of dysmenorrhea.

The β₃-agonist compounds for the use according to the invention are administered in pharmaceutical compositions prepared according to the conventional methods, such as disclosed, for example, in the abovementioned patents.

In order to obtain the desired therapeutic effect, the dose of active principle to be administered can vary between 0.01 and 100 mg per kg of body weight and per day, depending upon the seriousness of the symptoms.

Each unit dose can comprise from 0.1 to 500 mg of active principle, preferably in combination with a pharmaceutical vehicle. This unit dose can be administered 1 to 4 times daily.

What is claimed is:

1. A method for inhibiting uterine contractions which comprises administering to a patient requiring such treatment an effective amount of a β₃-agonist compound.

2. A method of preventing or slowing down premature labor which comprises administering to a patient requiring such treatment an effective amount of a β₃-agonist compound.

3. A method for the treatment and/or the prophylaxis of dysmenorrhea which comprises administering to a patient requiring such treatment an effective amount of a β₃-agonist compound.

4. A method according to any one of claims 1–3 wherein said β₃-agonist is a compound of formula (I)

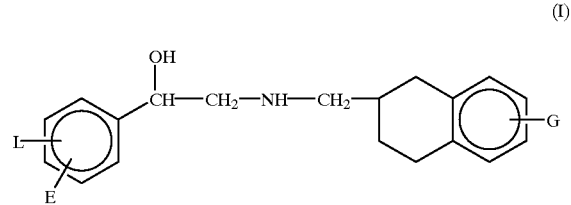

(I)

in which
E represents hydrogen, a (C₁–C₄)alkyl group, a (C₁–C₄) alkoxy group, a phenyl group, a nitro group, a halogen atom or a trifluoromethyl group, L represents hydrogen, a (C₁–C₄)alkyl group, a (C₁–C₄) alkoxy group, a phenyl group, a nitro group or a halogen atom, or E and L together represent a —CH=CH—CH=CH— or —CH₂—CH₂—CH₂—CH₂— group, and G represents hydrogen, a chlorine atom, a hydroxyl group or an OG' group where G' represents a (C₁–C₄)alkyl group which is unsubstituted or substituted by a hydroxyl, (C₁–C₄)alkoxy, (C₁–C₄)alkoxycarbonyl, carboxyl or (C₃–C₇)cycloalkyl group; a (C₃–C₇) cycloalkyl group; or a (C₂–C₄)alkanoyl group, or one of its pharmaceutically acceptable salts.

5. A method according to claim 4 wherein said β₃-agonist is chosen from N-[(6-hydroxy- 1,2,3,4-tetrahydronaphth-(2R)-2-yl)methyl]-(2R)-2-hydroxy-2-(3-chlorophenyl) ethanamine and N-[(7-methoxy-1,2,3,4-tetrahydronaphth-(2R)-2-yl)methyl]-(2R)-2-hydroxy-2-(3-chlorophenyl) ethanamine and their pharmaceutically acceptable salts.

6. A method according to any one of claims 1–3 wherein said β₃-agonist is chosen from the following products of formula (a) to (m):
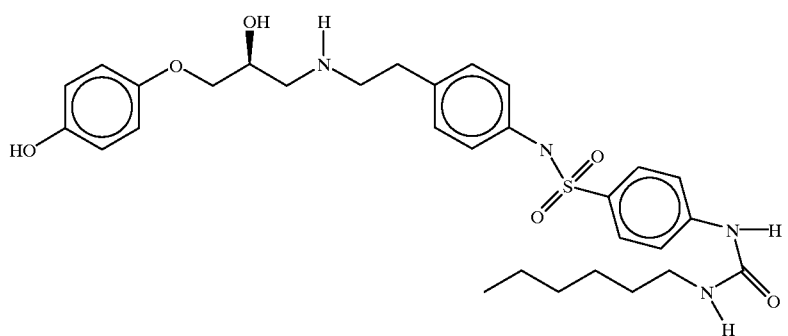
a
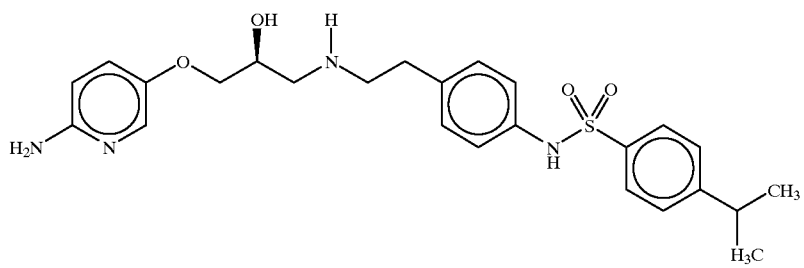
b
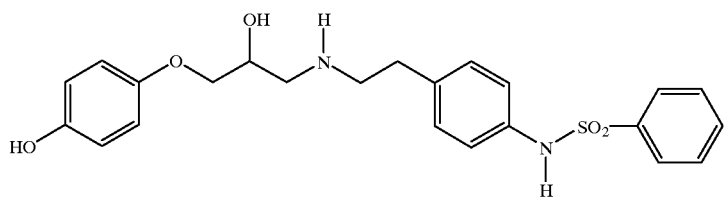
c
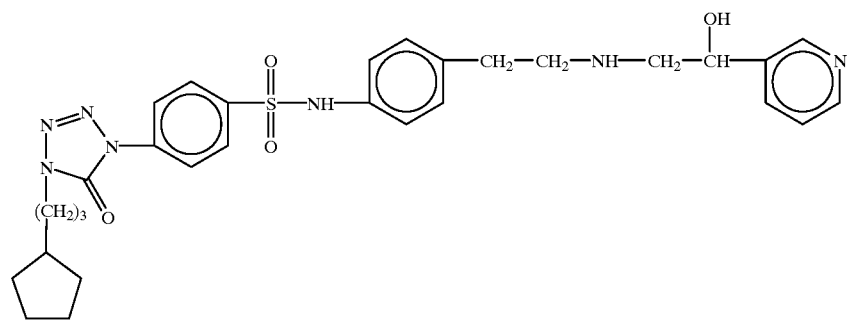
d -continued
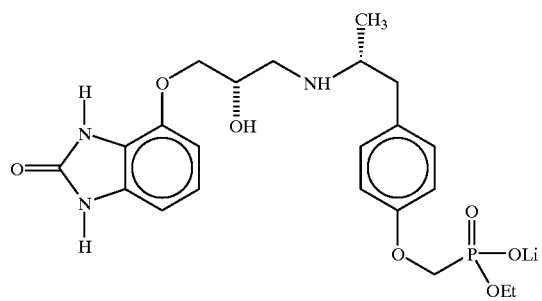
e
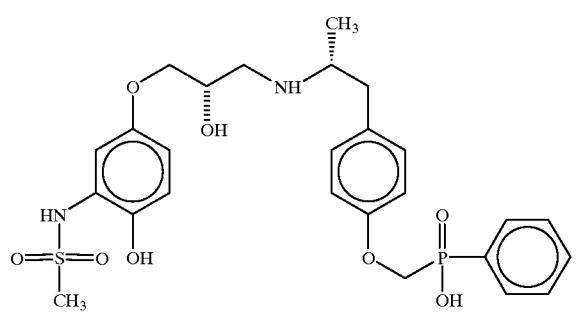
f
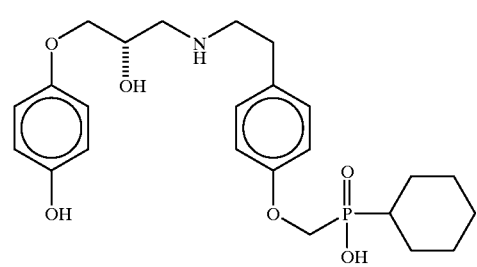
g
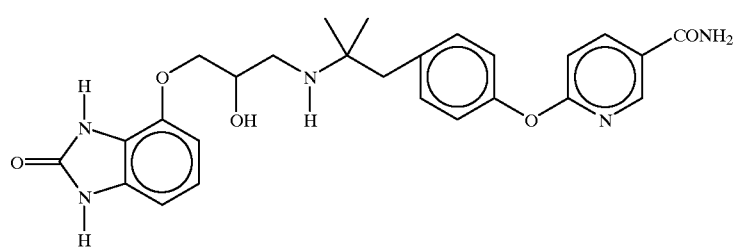
h
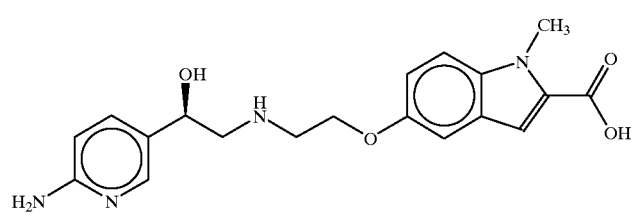
i
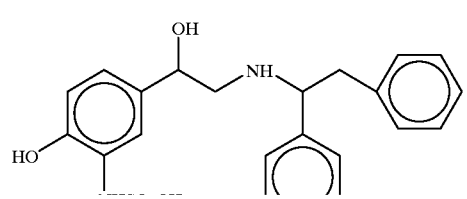
j

* * * * *

UNITED STATES PATENT AND TRADEMARK OFFICE
CERTIFICATE OF CORRECTION

PATENT NO.      : 6,310,050 B1                    Page 1 of 3
APPLICATION NO. : 09/807342
DATED           : October 30, 2001
INVENTOR(S)     : Advenier et al.

It is certified that error appears in the above-identified patent and that said Letters Patent is hereby corrected as shown below:

At Column 2:  line 16: "WO 94J29290" should read as -- WO 94/29290 --;
              line 37: "a ($C_1$-C4)alkyl" should read as -- a ($C_1$-$C_4$)alkyl --.

At Column 7:  line 54: "ethanamine," should read as -- ethanamine. --;
              line 63: "tetranhydronaphth" should read as -- tetrahydronaphth --;
              line 64: "3chlorophenyl" should read as -- 3-chlorophenyl --.

In Claim 6:   Columns 9-10, line 6, compound a:

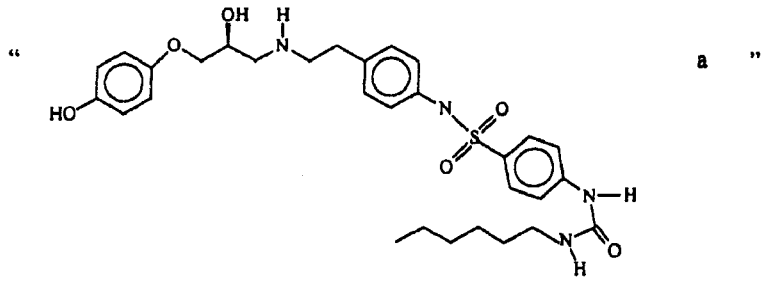

should read as

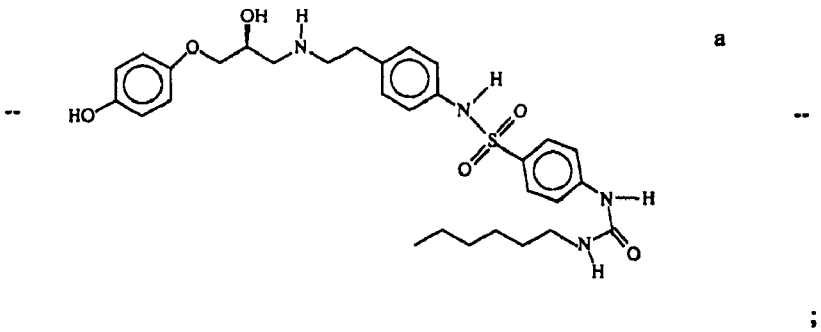

;

UNITED STATES PATENT AND TRADEMARK OFFICE
CERTIFICATE OF CORRECTION

PATENT NO. : 6,310,050 B1
APPLICATION NO. : 09/807342
DATED : October 30, 2001
INVENTOR(S) : Advenier et al.

It is certified that error appears in the above-identified patent and that said Letters Patent is hereby corrected as shown below:

In Claim 6: Columns 11-12, bottom line, compound j:

"  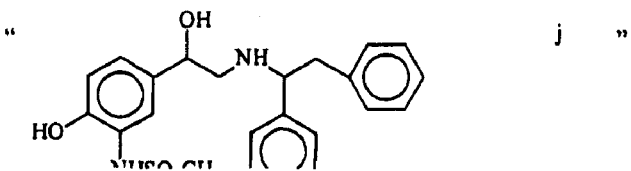  j  "

should read as:

--  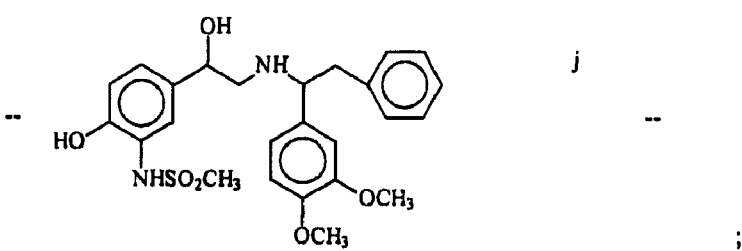  j  --

;

UNITED STATES PATENT AND TRADEMARK OFFICE
CERTIFICATE OF CORRECTION

PATENT NO.       : 6,310,050 B1
APPLICATION NO.  : 09/807342
DATED            : October 30, 2001
INVENTOR(S)      : Advenier et al.

It is certified that error appears in the above-identified patent and that said Letters Patent is hereby corrected as shown below:

In Claim 6: Columns 13-14, line 1, insert the following:

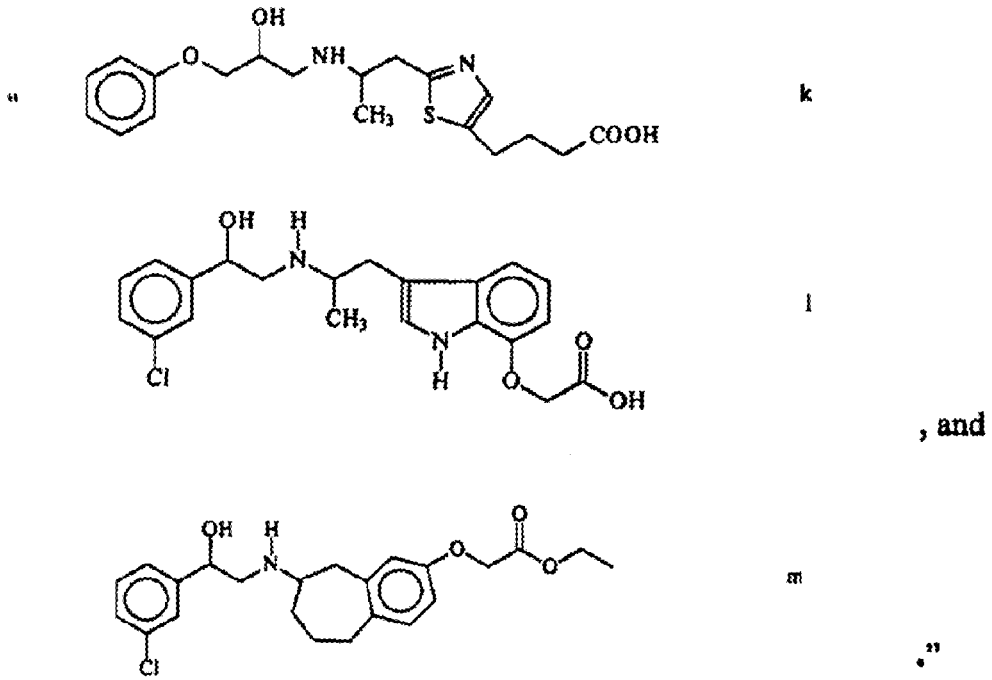

Signed and Sealed this

Eighth Day of January, 2008

JON W. DUDAS
*Director of the United States Patent and Trademark Office*